(12) United States Patent
Zhang

(10) Patent No.: US 9,197,082 B1
(45) Date of Patent: Nov. 24, 2015

(54) TECHNIQUES FOR POWER SOURCE MANAGEMENT USING A WRIST-WORN DEVICE

(71) Applicant: Jack Ke Zhang, Ijamsville, MD (US)

(72) Inventor: Jack Ke Zhang, Ijamsville, MD (US)

( * ) Notice: Subject to any disclaimer, the term of this patent is extended or adjusted under 35 U.S.C. 154(b) by 0 days.

(21) Appl. No.: 14/565,373

(22) Filed: Dec. 9, 2014

(51) Int. Cl.
| | |
|---|---|
| H02J 7/00 | (2006.01) |
| A61B 5/00 | (2006.01) |
| A61B 5/024 | (2006.01) |
| H02J 7/02 | (2006.01) |

(52) U.S. Cl.
CPC ............ *H02J 7/0027* (2013.01); *A61B 5/0022* (2013.01); *A61B 5/02438* (2013.01); *H02J 7/025* (2013.01)

(58) Field of Classification Search
USPC ......................................................... 320/108
See application file for complete search history.

(56) References Cited

U.S. PATENT DOCUMENTS

| | | | |
|---|---|---|---|
| 5,827,180 A | 10/1998 | Goodman | |
| 6,075,755 A | 6/2000 | Zarchan | |
| 6,443,906 B1 * | 9/2002 | Ting et al. | ..................... 600/490 |
| 7,162,368 B2 | 1/2007 | Levi et al. | |
| 7,285,090 B2 | 10/2007 | Stivoric et al. | |
| 8,217,795 B2 | 7/2012 | Carlton-Foss | |
| 8,457,367 B1 | 6/2013 | Sipe et al. | |
| 8,461,988 B2 | 6/2013 | Tran | |
| 8,708,903 B2 | 4/2014 | Tran | |
| 8,952,818 B1 | 2/2015 | Zhang | |
| 2002/0026330 A1 | 2/2002 | Klein et al. | |
| 2003/0052787 A1 | 3/2003 | Zerhusen et al. | |
| 2003/0060721 A1 | 3/2003 | Nakazawa et al. | |
| 2003/0176815 A1 | 9/2003 | Baba et al. | |
| 2003/0212379 A1 | 11/2003 | Bylund et al. | |
| 2004/0077934 A1 | 4/2004 | Massad | |
| 2005/0089197 A1 | 4/2005 | Iwasaki et al. | |
| 2005/0101845 A1 | 5/2005 | Nihtila et al. | |
| 2007/0197878 A1 | 8/2007 | Shklarski et al. | |
| 2007/0257636 A1 * | 11/2007 | Phillips et al. | ................ 320/108 |
| 2008/0086318 A1 | 4/2008 | Gilley et al. | |
| 2008/0129518 A1 | 6/2008 | Carlton-Foss et al. | |
| 2008/0162192 A1 | 7/2008 | Vonk et al. | |

(Continued)

FOREIGN PATENT DOCUMENTS

| | | |
|---|---|---|
| JP | 2007505412 | 3/2007 |
| KR | 1020020013214 | 2/2002 |

OTHER PUBLICATIONS

Blipcare , "Wi-Fi Blood Pressure", retrieved with the Wayback Machine with http://www.blipcare.com/blip-bp.html, Feb. 4, 2013, 4 pages.

*Primary Examiner* — Yalkew Fantu
(74) *Attorney, Agent, or Firm* — Kilpatrick, Townsend & Stockton LLP

(57) ABSTRACT

A method, apparatus, and/or system for patient wellness monitoring using a wrist-worn device is disclosed. The wrist-worn device may include a faceplate device and a wristband monitoring device. In one step, it may be determined that the faceplate device is detached from the wristband monitoring device. In response to the determination, the wristband monitoring device may operate on battery power. A sensor may be activated on the wristband monitoring device to collect vital sign information of a user. The vital sign information of the user may be wirelessly transmitted from the wristband monitoring device and received by the faceplate device. Upon determining that the faceplate device is attached to the wristband monitoring device, a battery on the wristband monitoring device may be charged.

20 Claims, 8 Drawing Sheets

(56) References Cited

U.S. PATENT DOCUMENTS

| | | |
|---|---|---|
| 2008/0266118 A1 | 10/2008 | Pierson et al. |
| 2009/0187121 A1 | 7/2009 | Evans et al. |
| 2009/0252311 A1* | 10/2009 | Kuiken .................... 379/102.02 |
| 2009/0318779 A1 | 12/2009 | Tran |
| 2009/0322513 A1* | 12/2009 | Hwang et al. ............ 340/539.12 |
| 2009/0322540 A1 | 12/2009 | Richardson et al. |
| 2009/0322548 A1 | 12/2009 | Gottlieb et al. |
| 2010/0010428 A1 | 1/2010 | Yu et al. |
| 2010/0076331 A1 | 3/2010 | Chan et al. |
| 2010/0152548 A1 | 6/2010 | Koski et al. |
| 2010/0194572 A1 | 8/2010 | Chan et al. |
| 2011/0093296 A1* | 4/2011 | Klink ................................ 705/3 |
| 2011/0230733 A1 | 9/2011 | Al-Ali et al. |
| 2011/0263950 A1 | 10/2011 | Larson et al. |
| 2012/0274464 A1 | 11/2012 | Sweeney et al. |
| 2013/0127980 A1 | 5/2013 | Haddick et al. |
| 2013/0169431 A1 | 7/2013 | Alhuwaishel et al. |
| 2013/0310658 A1 | 11/2013 | Ricks et al. |
| 2013/0318027 A1 | 11/2013 | Almogy et al. |
| 2013/0345530 A1 | 12/2013 | McRoberts et al. |
| 2014/0052464 A1 | 2/2014 | Ray |
| 2014/0163400 A1 | 6/2014 | Khanuja et al. |
| 2014/0247361 A1 | 9/2014 | Sarwar et al. |
| 2014/0275928 A1 | 9/2014 | Acquista et al. |
| 2014/0276552 A1 | 9/2014 | Nguyen et al. |
| 2014/0375246 A1* | 12/2014 | Boysen et al. ................. 320/101 |
| 2014/0378786 A1 | 12/2014 | Hong et al. |

\* cited by examiner

US 9,197,082 B1

TECHNIQUES FOR POWER SOURCE MANAGEMENT USING A WRIST-WORN DEVICE

BACKGROUND

This disclosure relates in general to power source management and, but not by way of limitation, to systems and methods that are used to manage the power source of devices used to monitor the wellness of a patient.

In the United States, it is estimated that 32 million people use three or more medications daily. 67 million, or 31 percent, of American adults have high blood pressure. 29 million, or 9.3 percent, of people in the United States are diabetic. The medical cost of obesity in the United States in 2008 alone was approximately $147 billion. The statistics are staggering as more and more individuals find themselves in need of medical treatment.

A patient undergoing medical treatment may often be prescribed one or more therapies by his or her physician. Unfortunately, many people who are undergoing treatment do not follow the regimen as directed by their doctor or pharmacist. In fact, as many as 75% of patients fail to adhere to, or comply with, physician-prescribed treatment regimens. Non-adherence examples include, but are not limited to, failing to take a medication, failing to take various sensor (e.g., blood pressure, heart rate, glucose) readings, failing to exercise, to name a few. Monitoring a patient's overall wellness is difficult for medical personnel as patient data is typically collected and available to the medical personnel only when the patient avails himself to a doctor's office or hospital.

Current techniques related to self-monitoring wellness using a monitoring device are lacking with respect to power management. For example, a patient may have to remove a body-worn device in order to charge the device. During charging, the device may not be monitoring the user. This is especially detrimental to the user who may be using the device to actively monitor serious health concerns.

SUMMARY

In one example embodiment, the present disclosure provides a wrist-worn device for managing patient wellness. The wrist-worn device includes one or more processors and one or more memories coupled with the one or more processors. The one or more processors and one or more memories are configured to perform operations. The operations include receiving, by the wrist-worn device, a therapy for a user. The therapy may specify one or more treatments selected by a care provider. A regimen may be determined, by the wrist-worn device, for the user based on the therapy. A sensor on the wristband monitoring device may be activated to collect vital sign information of a user. Vital sign information of the user may be received by the faceplate device, from the wristband monitoring device. The wristband monitoring device may be caused to operate on battery power when it is determined that the faceplate device is detached from the wristband device. A battery on the wristband monitoring device may be charged when it is determined that the faceplate device is attached to the wristband monitoring device. The vital sign information may be wirelessly transmitted away from the wrist-worn device.

In another example embodiment, the present disclosure provides a computer-implemented method for managing patient wellness with a wrist-worn device. The method includes determining that the faceplate device is detached from the wristband monitoring device. In response to the determination, the wristband monitoring device may operate on battery power. A sensor may be activated on the wristband monitoring device to collect vital sign information of a user. The vital sign information of the user may be wirelessly transmitted from the wristband monitoring device and received by the faceplate device. Upon determining that the faceplate device is attached to the wristband monitoring device, a battery on the wristband monitoring device may be charged.

In yet another example embodiment, the present disclosure provides a non-transitory computer-readable storage medium for managing patient wellness having computer-executable instructions stored thereon that, when executed by a processor, cause the processor to perform operations. The operations include determining that the faceplate device is detached from the wristband monitoring device. In response to the determination, the wristband monitoring device may be caused to operate from an alternative power source. A sensor on the wristband monitoring device may be activated to collect vital sign information of a user. The vital sign information of the user may be wirelessly transmitting from the wristband monitoring device and received by the faceplate device. The vital sign information may be wirelessly transmitted away from the wrist-worn device.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

Figure 1:
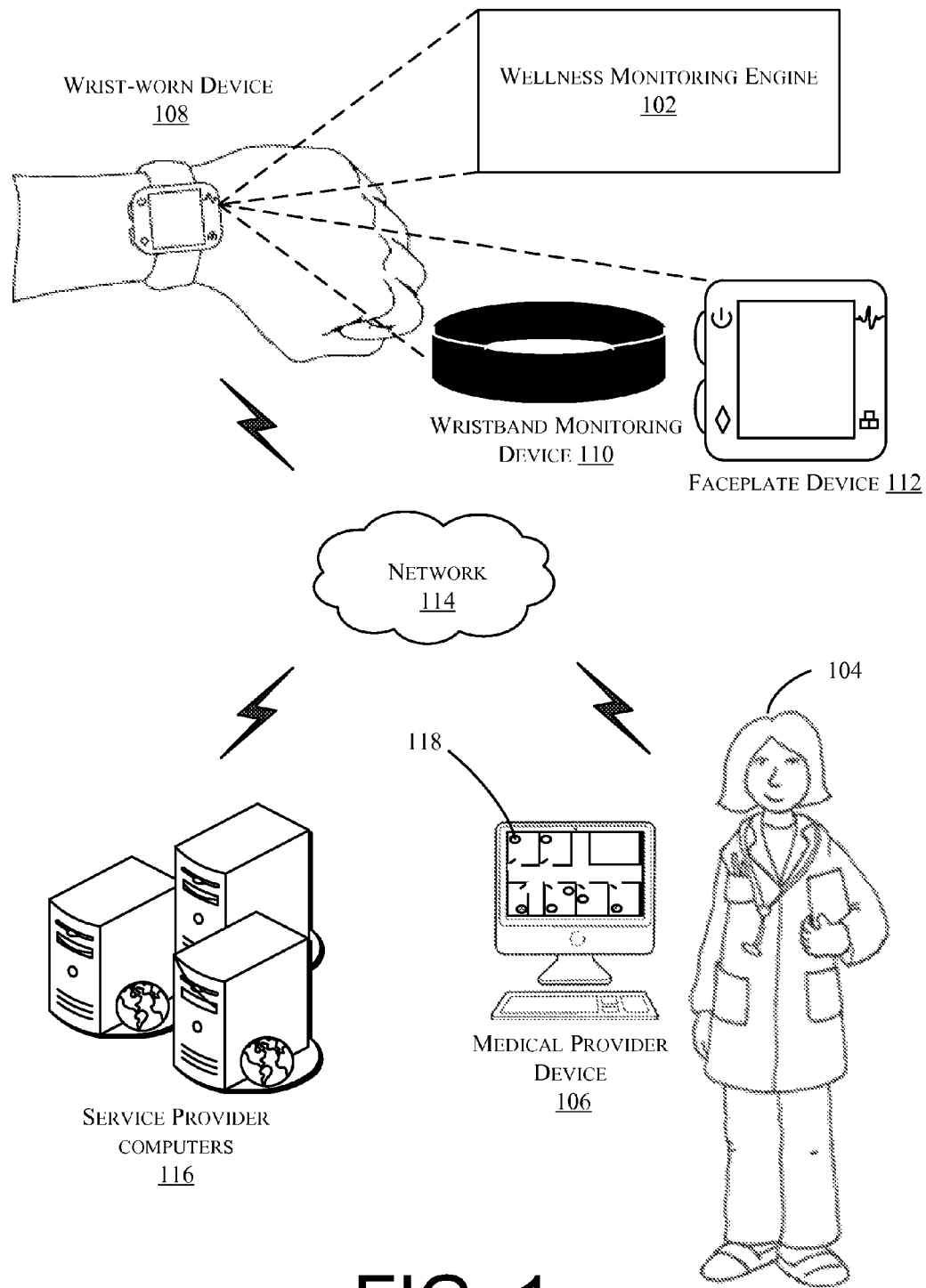
FIG. 1 depicts an example environment of an embodiment of a power management engine included in a wellness monitoring engine.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims. Specific details are given in the following description to provide a thorough understanding of the embodiments. However, it will be understood by one of ordinary skill in the art that the embodiments may be practiced without these specific details.

As described in the background of this disclosure, embodiments of the present invention comprise methods for monitoring patient wellness. Specifically, these methods include the use of a wrist-worn device. The wrist-worn device may include one or many sensors that may be used to track vital signs and/or locational information of the patient. As used herein, a "sensor" may comprise an accelerometer, a gyroscope, a blood-oxygen level monitor, heart-rate monitor, a blood pressure monitor, a glucose monitor, a thermometer, a global positioning system (GPS) device, a pedometer, or an altimeter. Additionally, the device may be capable of presenting notification to the user. These notifications may be audible, haptic, graphical, or textual in nature. The wrist-worn device may include a wristband monitoring device connected to a faceplate device for caring out the features described herein. The wristband monitoring device has a number of sensors located on the band to measure various vital signs, and visual indicators (e.g., LED lights) to indicate charging and sensor activation. The faceplate device includes a number of sensors, a wireless transmitter, a battery charger, and a user interface (e.g., a touch screen) for interacting with the user and remote systems.

Generally speaking, embodiments of the present invention enable a patient to more effectively adhere to a physician-prescribed therapy using the wrist-worn device described above. Additionally, these embodiments enable ongoing monitoring of a patient's overall wellness.

Embodiments for the present invention comprise wrist-worn devices and methods for managing patient wellness. In at least one example, a wrist-worn device (e.g., a watch) is preconfigured with information regarding at least one therapy. For instance, the watch is preconfigured to be used for a blood pressure therapy. As used herein, a "therapy" may include one or more medical treatments including, but not limited to, one or more prescribed medications, one or more physical activities, one or more sensor reading requirements, or any combination of the above. In at least one example, information is loaded onto the watch by a physician, a pharmacist, or another service provider. The pre-loaded information is then used to determine a regimen to be followed. A "regimen," as used herein, is intended to mean a schedule specifying at least one situation for which at least one event associated with one or more therapies should be performed. For instance, a regimen may indicate that an event (e.g. medication intake, exercise commencement, sensor reading commencement) should occur at pre-determined periodic times.

Consider the case where a patient is diagnosed with high blood pressure. His physician prescribes medication A and instructs the patient to take 500 mg of medication A, twice daily, once in the morning, once in the evening, with each dose to be taken shortly after a meal. Additionally, the physician instructs the patient to take his own blood pressure and document the results 3 times daily, equally spanned over the course of the day. In this example, the physician preconfigures a watch with this therapy. A regimen schedule is generated by the watch based on the therapy. The regimen defines at least one day and time during which the patient should take his 500 mg of medication A. The regimen can further define when blood pressure readings may be taken. The watch can generate reminders for the users based on the regimen. Additionally, the watch may stimulate sensor reading intake based on the regimen or by user-initiation.

In accordance with at least one embodiment, the watch receives user input indicating compliance with the therapy. For instance, continuing with the previous example, the user is reminded to eat prior to taking his medication. Subsequent to the reminder being presented to the user, the user may be prompted for input. The prompt may be included in the reminder or may exist as a separate prompt. In at least one example, the reminder constitutes a textual message presented on the faceplate device and/or an audible alert sounded by the faceplate device. The user acknowledges the reminder by dismissing the reminder and/or turning off the audible sound. In some cases, dismissing the reminder and/or turning off the audible sound may be considered user input indicating compliance with the reminder. In at least one example, the user is queried regarding his compliance. For instance, the user is posed the question "did you eat a meal?" The user enters input indicating either that he did eat a meal, or alternatively, that he did not eat a meal. In at least one example, a Bluetooth device is used to enter user input indicating compliance with the reminder. For instance, a medication container having Bluetooth communication capabilities sends, to the watch, an indication that the medication container has been opened. This indication, alone or in combination with the reminder information, constitutes user input indicating that the user has complied with taking his medication.

In accordance with at least one embodiment, the watch generates reminder events at the time the patient is supposed to take the medication. The user responds in a similar fashion as described above, by dismissing the reminder, turning off the audible sound, or affirmatively answering a question posed by the device. In at least one example, the regimen dictates that the watch query the user with a question some period of time after the user has indicated that he has taken the medication. For instance, the user enters compliance input indicating that he has taken his blood pressure medication. The regimen specifies that one hour after receipt of the user compliance input the user be asked, "Are you feeling dizzy?" The user makes a selection on the watch indicating a response to the question. The response is recorded by the watch and reported, wirelessly, away from the watch (e.g., to a server responsible for storing such information), or alternatively, stored on the watch.

In at least one embodiment, the regimen causes a blood pressure sensor to be activated some period after the user compliance input has been received, and/or at another suitable time as defined by the regimen. The period between sensor activations may vary depending on the therapy and may further depend on user input. For example, the device may pose a question to the user to determine whether to initiate the sensor reading. For instance, the device poses the question "are you ready to take your blood pressure?" In at least one example, the user is required to indicate agreement before the sensor reading commences. Alternatively, the watch may initiate a sensor reading without user interaction. The watch records any sensor readings taken and reports the sensor readings away from the watch (e.g., to a server responsible for storing such information). Alternatively, the watch may store such sensor readings on the wrist-worn device.

In accordance with at least one embodiment, previously received user input is used to modify a regimen. User input, as described above, includes user actions taken in response to presented reminders, user actions taken regarding Bluetooth-enabled containers, user responses to questions posed by the watch, and/or a lack of a user response. User input may be recorded by the watch at any suitable time. In at least one example, the watch reports user input electronically to a physician and/or pharmacist, for example. This report may be reported in an email message, a text message, or any suitable type of electronic communication. Based on the report, or at any suitable time, the physician and/or pharmacist modify the prescribed therapy. This modification is electronically communicated to the watch. In response to the modification, the watch alters the therapy and/or regimen to reflect the modification. Additionally, or alternatively, the watch modifies the regimen based on the received user responses in accordance with the therapy. For instance, the therapy is configured to adjust medication in response to a certain one or more user inputs. In one illustrative example, the regimen indicates that the user take 500 mg of medication A once a day. However, the user is posed a question such as "do you feel dizzy?" at some point in therapy, in accordance with the current regimen. The user indicates that he feels dizzy. Based on the affirmative response, the watch automatically modifies the regimen such that the user is prompted to take another 500 mg dose of medication A. Alternatively, the watch indicates to the user that he should refrain from taking any more medication. A variety of modifications may be determined and would depend on the particular therapy being implemented and the user input received.

In accordance with at least one embodiment, a user may detach a faceplate device on the wrist-worn device from a wristband device in order to charge the faceplate device (e.g., via A/C adaptor, via proximity charging or inductive charging techniques including magnetic or acoustic methods). While the faceplate device is charging, the user may wear and operate the wristband device. While detached, the wristband monitoring device and faceplate monitoring device may still communicate with one another wirelessly (e.g., via Bluetooth). During such time, the wristband device may operate using a power source located on the wristband device (e.g., a battery). When the faceplate device has charged, the user may reattach the faceplate device to the wristband device. Upon reattachment, a power source located on the wristband monitoring device may charge from a power source located on the faceplate device.

Referring now to the drawings, in which like reference numerals represent like parts, FIG. 1 depicts an example environment of an embodiment 100 of a power management engine included in a wellness monitoring engine. The wrist-worn device 108 can include a wellness monitoring engine 102. The wellness monitoring engine 102 may include a power management engine 103. In accordance with at least one embodiment, the wrist-worn device 108 may be preconfigured with a prescribed therapy (e.g., by a medical provider). The wrist-worn device may include a wristband monitoring device 110 and a faceplate device 112. The wrist-worn device 108 utilizes one or more sensors (e.g., on the wristband monitoring device 110) to monitor the patient's vital signs according to the regimen. The wrist-worn device 108 enables interaction between the wellness monitoring engine 102 and the user. The wrist-worn device 108 may be used to illicit user input, to display information to the user, to wirelessly transmit patient data to service provider computers 116, and to receive information or data from service provider computers 116.

In at least one embodiment, the wellness monitoring engine 102 is a component of the wrist-worn device 108. Service provider computers 116 includes one or more computing devices responsible for storing and/or managing medical-related data associated with the patient. Service provider computers 116 may communicate wirelessly with wellness monitoring engine 102 to provide information regarding the therapy via a network 114. This information includes therapy configuration. Additionally, as described above, the medical provider 104 can utilize the medical provider device 406 to modify a therapy. Such modifications are communicated to service provider computers 116 via the network 114. Service provider computers 116 records such modifications and communicates the modifications to wellness monitoring engine 102. Wellness monitoring engine 102 generates a new regimen or, alternatively, alters an existing regimen in accordance with the modifications.

In some embodiments network 114 is a cellular network. Wrist-worn device 108 may exchange cellular network control, timing and status information with a cellular network access point so as to maintain communication capabilities in the cellular network. Cellular network access points may provide access to the internet or other data networks. The wrist-worn device 108 may establish an internet connection by detecting a cellular access point, performing joining procedures, and regularly exchanging status, control and routing information with the access point. The wrist-worn device 108 may use the internet connection to access weather data, GPS data, or to communicate with other devices described herein.

In at least one embodiment, wristband monitoring device 110 may be operated separately from faceplate device 112. For example, a user, wanting to sleep with a less bulky apparatus, may detach faceplate device 112 from wristband monitoring device 110. While detached, the faceplate device 112 may be charged via a charging dock, an A/C adaptor, inductive charging using magnetic or acoustic methods, or any suitable means for charging an electronic device. While detached, faceplate device 112 and wristband monitoring device 110 may continue communicating (e.g., via Bluetooth). For example, perhaps user's regimen specifies that blood pressure readings are to be taken every three hours. Faceplate device 112 may continue to activate sensors on wristband monitoring device 110 according to the regimen. Accordingly, wristband monitoring device 110 may wirelessly transmit (e.g., via Bluetooth) vital sign information to faceplate device 112. While detached, wristband monitoring device 110 may be configured to run on an alternate power source (e.g., a battery located on wristband monitoring device 110). When reattached, faceplate device 112 may serve as a charging source (e.g., via inductive charging) for wristband monitoring device 110. In this manner, the user may continue to have his vital signs monitored while wearing only the wristband monitoring device 110. Additionally, wristband monitoring device 110 is configured to be charged from faceplate device 112 without the need to remove wristband monitoring device 110 from the user.

Figure 2:
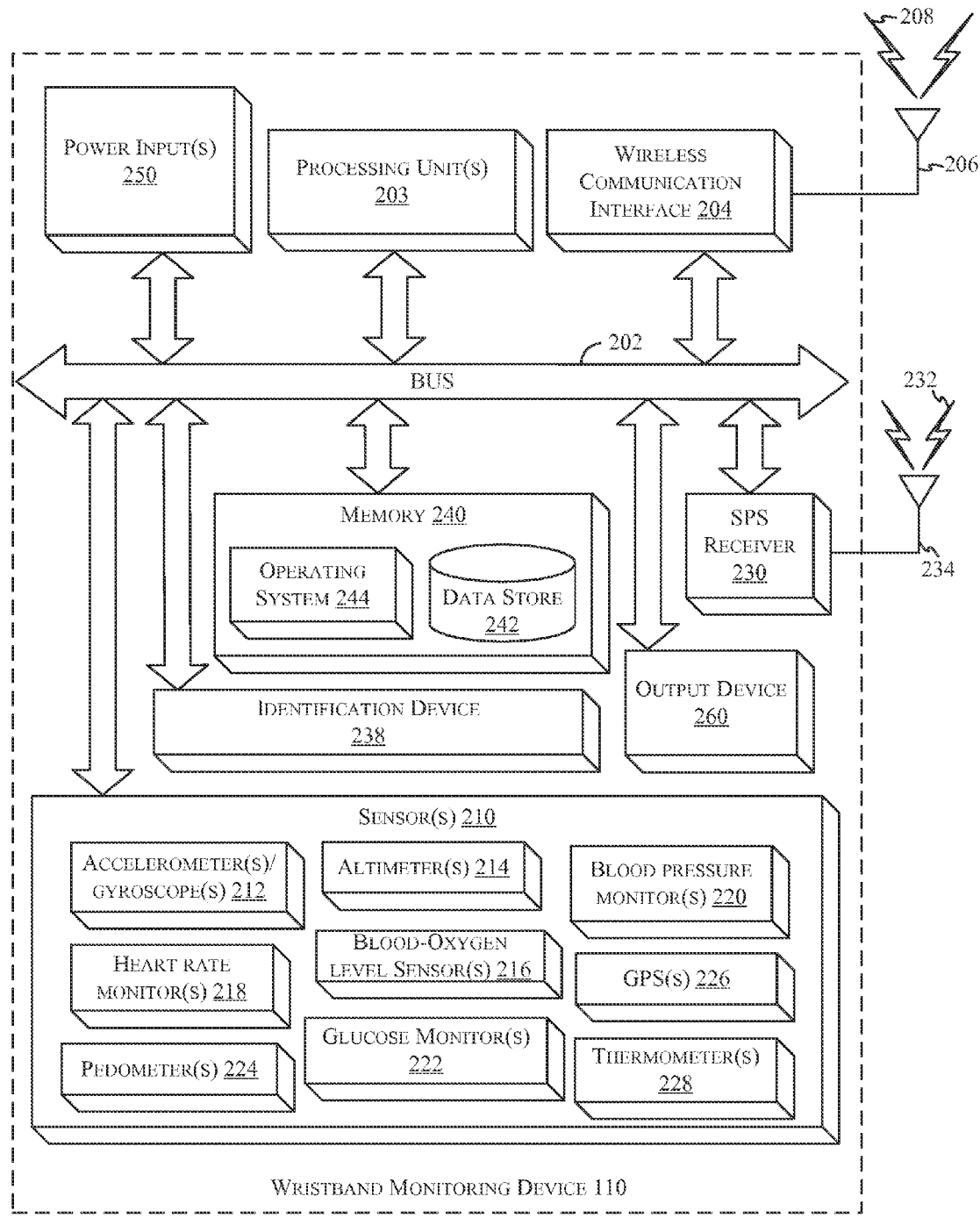
FIG. 2 depicts an example wristband monitoring device for use with the wellness monitoring engine, in accordance with at least one embodiment.

FIG. 2 depicts an example of the wristband monitoring device 110 of the wrist-worn device 108. It should be noted that FIG. 2 is meant only to provide a generalized illustration of various components, any or all of which may be utilized as appropriate. In some embodiments, some or all of the components included in the wristband monitoring device 110 may also or instead be located on the faceplate device 112. Moreover, system elements may be implemented in a relatively separated or relatively more integrated manner.

The wristband monitoring device 110 is shown comprising hardware elements that can be electrically coupled via a bus 202 (or may otherwise be in communication, as appropriate). The hardware elements may include a processing unit(s) 203 which can include without limitation one or more general-purpose processors, one or more special-purpose processors (such as digital signal processors (DSPs), application specific integrated circuits (ASICs), and/or the like), and/or other processing structure or means, which can be configured to perform one or more of the methods described herein.

The wristband monitoring device 110 might also include a wireless communication interface 204, which can include without limitation a modem, a network card, an infrared communication device, a wireless communication device, and/or a chipset (such as a Bluetooth device, an IEEE 802.11 device, an IEEE 802.15.4 device, a Wi-Fi device, a WiMax device, cellular communication facilities, etc.), and/or the like. The wireless communication interface 204 may permit data to be exchanged with a network, wireless access points, other computer systems, and/or any other electronic devices described herein. The communication can be carried out via one or more wireless communication antenna(s) 206 that send and/or receive wireless signals 208. In at least one embodiment, wristband monitoring device 110 may communicate with faceplate device 112 via the wireless communication interface 204.

Depending on desired functionality, the wireless communication interface 204 can include separate transceivers to communicate with base transceiver stations (e.g., base transceiver stations of a cellular network) and access points. These different data networks can include, an Orthogonal Frequency-Division Multiple Access (OFDMA), Code Divisional Multiple Access (CDMA), Global System for Mobile Communications (GSM)), and/or other types of networks.

The wristband monitoring device 110 can further include sensor(s) 210. Such sensors can include, without limitation, one or more accelerometer(s) and/or gyroscope(s) 212, altimeter(s) 214, blood-oxygen level sensor(s) 216, heart rate monitor(s) 218, blood pressure monitor(s) 220, glucose monitor(s) 222, pedometer(s) 224, GPS(s) 226, thermometer(s) 228, and the like. At least a subset of the sensor(s) 220 can provide readings used to provide wellness monitoring as described herein.

Embodiments of wristband monitoring device 110 may also include a Satellite Positioning System (SPS) receiver 230 capable of receiving signals 232 from one or more SPS satellites using an SPS antenna 234. Such positioning can be utilized to complement and/or incorporate the techniques described herein. The SPS receiver can receive satellite data that can be transmitted to the GPS sensor 226. The satellite data can be information sufficient to allow the GPS sensor 226 to determine a geographic location of the wristband monitoring device based on the satellite data. It can be noted that, as used herein, an SPS may include any combination of one or more global and/or regional navigation satellite systems and/or augmentation systems, and SPS signals may include SPS, SPS-like, and/or other signals associated with such one or more SPS.

Embodiments of wristband monitoring device 110 may also include an identification device 238. Identification device 238 may include a device that utilizes radio-frequencies in communication (e.g., a radio-frequency identification (RFID) device). A RFID device is a device that uses electromagnetic fields to transfer data for the purposes of automatically identifying and tracking tags attached to objects, the tags containing electronically stored information. Other identification devices may be utilized, including, but not limited to devices utilizing near field communication (NFC). NFC is a set of standards used by smartphone and similar devices to establish radio communication with each other by touching them together or bring them into proximity of one another. In at least one embodiment, The wristband monitoring device 110 may further include or be in communication with a memory 240. The memory 240 is an example of a computer-readable storage media. In at least one example, computer-readable storage media include volatile or non-volatile, removable or non-removable, media implemented in any method or technology for storage of information such as computer-readable instructions, data structures, program modules, or other data. Additional types of computer storage media that may be included in the wristband monitoring device 110 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the wristband monitoring device 110. Combinations of any of the above should also be included within the scope of computer-readable media. Memory 240 can further be used to store sensor data for any combination of sensors 210 in data store 242. Additionally, or alternatively memory 240 may be used to store medical-related data for the user.

Turning to the contents of the memory 240 in more detail, the memory 240, in at least one embodiment, includes an operating system 244 and one or more application programs, modules, or services for implementing the features disclosed herein including at least the perceived latency, such as via the wristband monitoring device 110 or dedicated applications. In at least one example embodiment, the wristband monitoring device 110 is configured to receive, store, and/or display content and at least one interface for interacting with the service provider computers 116 and/or user. Additionally, the memory 240 stores access credentials and/or other user information such as, but not limited to, user IDs, passwords, and/or other user information. In some examples, the user information includes information for authenticating an account access request such as, but not limited to, a device ID, a cookie, an IP address, a location, or the like. Additionally, the user information may include medical-related data associated with the user.

As used herein, medical-related data can include, for example, health information that is created or received by a health care provider, a processed or unprocessed version of medical data detected by medical equipment, and/or user-identified data. Medical-related data can include information that identifies a patient, such as personal information and/or demographic information. For example, the information can identify a patient's name, age, sex, race, physical address, phone number, email address and/or social security number. Medical-related data may include information collected by a health plan, a public health authority, an employer, a life insurer, a school or university, or a health care clearinghouse that relates to the past, present, or future physical or mental health or condition of any individual.

Medical-related data can include financial and/or insurance information corresponding to the patient. For example, the information can identify an insurance company, insurance plan, member identification number, group number, insurance contact information (e.g., address and/or phone number), deductible information, out-of-pocket information, copay information, an employer, an occupation and/or salary information.

Medical-related data can include medical-history information, such as past diagnoses, past or present symptoms or past procedures and/or corresponding dates (e.g., of diagnoses, symptom initiations and/or procedures). Medical-related data can identify past or present medications being taken by or having been prescribed to the patient and corresponding dates. In some examples, the medical-related data can identify orders pharmacology orders, whether associated with a patient, doctor, or otherwise.

Medical-related data can include an identification of one or more medical services being or having been requested by a patient. A medical service can include, for example, an evaluation performed by a medical care professional, a medical test, a surgery and/or other procedure. Medical-related data can identify a medical test or analysis that was performed or prescribed and/or a result of the test or analysis. For example, information can indicate that a test (e.g., lab test, MRI, x-ray, CT scan, echocardiography, EKG, EEG, EMG, or ultrasound) was performed on a particular date and/or by a particular entity and can further include a processed and/or unprocessed result of the test (e.g., a count or level; an indication as to whether a test result is normal; and/or an indication as to whether a particular feature (e.g., a fracture, tumor, lesion, slowed nerve conduction) was observed and/or a magnitude of the feature).

Medical-related data can identify one or more care providers or institutions. The care provider and/or institution can be one associated with recent or past care and/or with the patient. For example, data can be transmitted for a patient admitted in Hospital A and being treated by Specialist B, though the data can also identify that the patient's primary care physician is Doctor C.

Medical-related data can identify one or more emergency contacts or family members and contact data for the individuals. For example, medical-related data can identify that the patient's emergency contact is an adult child that may be contacted at a provided phone number.

Medical-related data can identify a patient healthcare directive. For example, medical-related data can identify if the patient has a living will, a do not resuscitate order (DNR), or if another individual has the right to make medical decisions relating to the patient's medical care.

Medical-related data may further include one or more authorized viewers. Authorized viewers are those that the user has agreed to allow access to his medical-related data. For example, a user may authorize a doctor, an individual having rights to make medical decision related to the patient's medical care, a medical institution, and the like to access his medical-related data. The user may indicate that the authorization is contingent on certain events transpiring (e.g., an emergency situation).

Medical-related data may, or may not, selectively pertain to a particular patient. For example, non-patient-specific data may include a price of a prescription, a recommended or approved dosing schedule for a medication, a work schedule for a physician, an acceptance criteria for a clinical study, Non-patient-specific data can include information pertaining to the operation of a medical care facility, financial information, administrative information, and generic clinical information.

Medical-related data can, depending on the implementation, include individually identifiable health information and/or de-identified information. Individually identifiable health information includes, for example, health information, including demographic information collected from an individual that is created or received by a health care provider, health plan, employer, or health care clearinghouse; and that relates to the past, present, or future physical or mental health or condition of an individual, the provision of health care to an individual, or the past, present, or future payment for the provision of health care to an individual; and that identifies the individual; or, with respect to which there is a reasonable basis to believe, can be used to identify the individual. De-identified information includes information that cannot be used on its own or with other information to identify a person to whom the information belongs. De-identified information can include normal ranges or values associated with various sensor data based on gender, age, or other classification. De-identified information can also include medical-related data aggregated from other wrist-worn device users or non-users related.

As used herein, medical-related data can include protected health information, which can include individually identifiable health information that is transmitted by electronic media, maintained in electronic media, or transmitted or maintained in any other form or medium. Examples of protected health information, include, for example any information about health status, provision of health care, or payment that can be linked to a particular patient and may include any of the following information capable of identifying the patient: names, geographic identifiers, dates directly relating to the patient, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

The memory 240 of the wristband monitoring device 110 also can comprise software elements (not shown), device drivers, executable libraries, and/or other code, such as one or more application programs, which may comprise computer programs provided by various embodiments, and/or may be designed to implement methods, and/or configure systems, provided by other embodiments, as described herein.

The wristband monitoring device 110 includes a output device 260. Output device 260 may include LED lights or other visual or audible indicators. The output device 260 may be used to indicate when a sensor is activated, when a reading is being taken, when the wristband monitoring device 110 is being charged, when the wristband monitoring device 110 is low on power, and the like.

The wristband monitoring device 110 includes a power source, and a means to charge said power source, indicated by power input(s) 250. In at least one embodiment, wristband monitoring device 110 may be connected to faceplate device 112 and the power source of the wristband monitoring device 110 may be charged (e.g., via inductive charging including magnetic or acoustic methods) from the battery of faceplate device 112. The power source may include a battery, a capacitor, or any other suitable means for storing chemical or electrical energy for later use.

Figure 3:
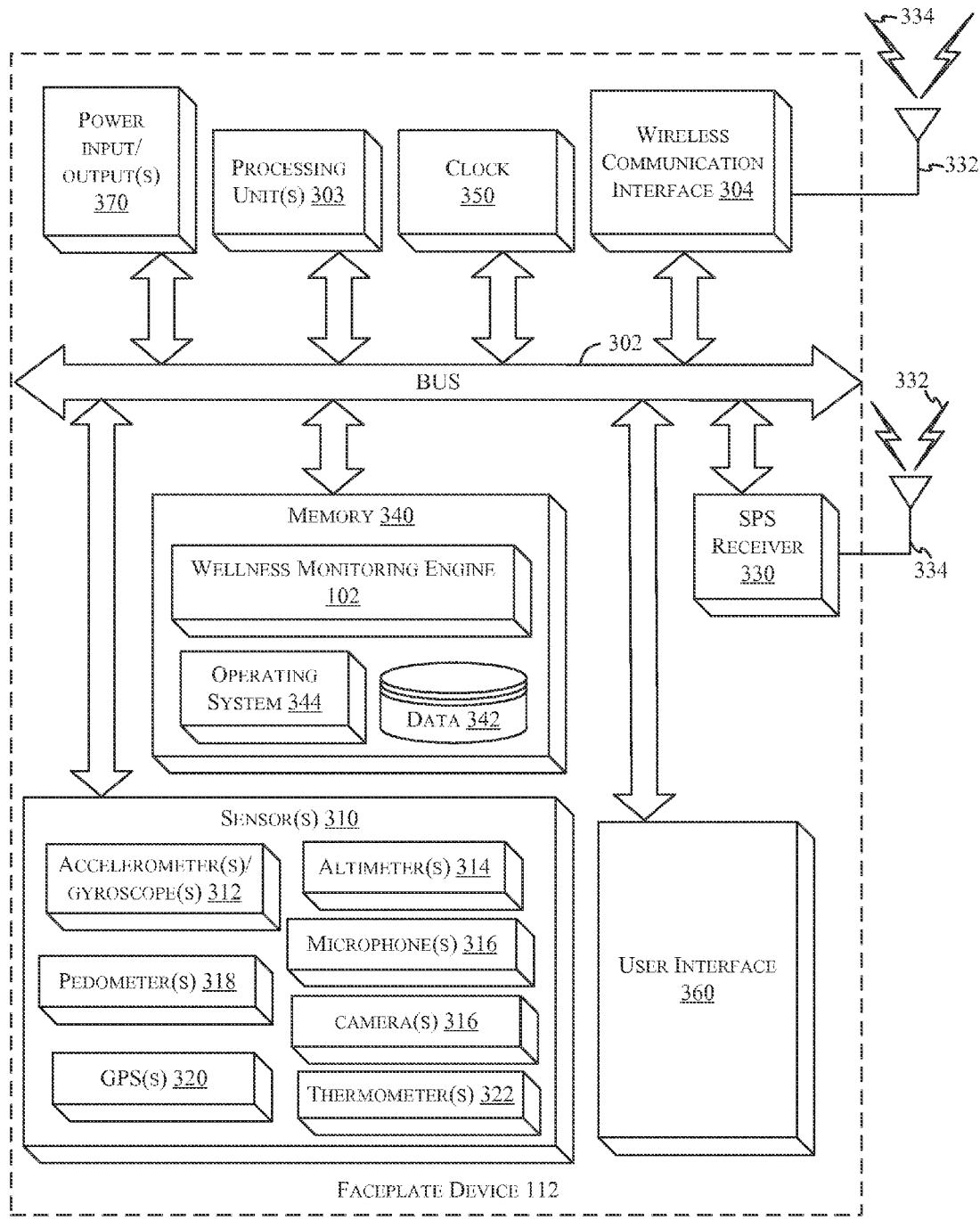
FIG. 3 depicts an example faceplate device for use with the wellness monitoring engine, in accordance with at least one embodiment.

FIG. 3 depicts an example faceplate device (e.g., faceplate device 112) of wrist-worn device 108, in accordance with at least one embodiment. Faceplate device 112 can implement the wellness monitoring techniques discussed herein. It should be noted that FIG. 3 is meant only to provide a generalized illustration of various components, any or all of which may be utilized as appropriate. In some embodiments, some or all of the components included in the faceplate device 112 may also or instead be located on the wristband monitoring device 110. Moreover, system elements may be implemented in a relatively separated or relatively more integrated manner.

The faceplate device 112 is shown comprising hardware elements that can be electrically coupled via a bus 302 (or may otherwise be in communication, as appropriate). The hardware elements may include a processing unit(s) 310 which can include without limitation one or more general-purpose processors, one or more special-purpose processors (such as digital signal processors (DSPs), application specific integrated circuits (ASICs), and/or the like), and/or other processing structure or means, which can be configured to perform one or more of the methods described herein.

The faceplate device 112 might also include a wireless communication interface 304, which can include without limitation a modem, a network card, an infrared communication device, a wireless communication device, and/or a chipset (such as a Bluetooth device, an IEEE 802.11 device, an IEEE 802.15.4 device, a Wi-Fi device, a WiMax device, cellular communication facilities, etc.), and/or the like. The wireless communication interface 304 may permit data to be exchanged with a network, wireless access points, other computer systems, and/or any other electronic devices described herein (e.g. the wristband monitoring device 110). The communication can be carried out via one or more wireless communication antenna(s) 306 that send and/or receive wireless signals 308. For example, the wireless signals 308 can be cellular network signals or a Bluetooth connection. In at least one embodiment, wristband monitoring device 110 may communicate with faceplate device 112 via the wireless communication interface 304.

Depending on desired functionality, the wireless communication interface 304 can include separate transceivers to communicate with base transceiver stations (e.g., base transceiver stations of a cellular network) and access points. These different data networks can include, an Orthogonal Frequency-Division Multiple Access (OFDMA), Code Divisional Multiple Access (CDMA), Global System for Mobile Communications (GSM), and/or other types of networks.

The faceplate device 112 can further include sensor(s) 310. Such sensors can include, without limitation, one or more accelerometer(s) and/or gyroscope(s) 312, altimeter(s) 314, microphone(s) 316, pedometer(s) 318, GPS(s) 320, thermometer(s) 322, and the like. At least a subset of the sensor(s) 310 can provide readings used to provide wellness monitoring as described herein.

Embodiments of wristband monitoring device 110 may also include a Satellite Positioning System (SPS) receiver 330 capable of receiving signals 332 from one or more SPS satellites using an SPS antenna 334. The SPS receiver can receive satellite data that can be transmitted to the GPS sensor 320. The satellite data can be information sufficient to allow the GPS sensor 320 to determine a geographic location of the wristband monitoring device based on the satellite data. Such positioning can be utilized to complement and/or incorporate the techniques described herein. It can be noted that, as used herein, an SPS may include any combination of one or more global and/or regional navigation satellite systems and/or augmentation systems, and SPS signals may include SPS, SPS-like, and/or other signals associated with such one or more SPS.

The faceplate device 112 may further include or be in communication with a memory 340. The memory 340 is an example of a computer-readable storage media. In at least one example, computer-readable storage media include volatile or non-volatile, removable or non-removable media implemented in any method or technology for storage of information such as computer-readable instructions, data structures, program modules, or other data. Additional types of computer storage media that may be included in the faceplate device 112 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the faceplate device 112. Combinations of any of the above should also be included within the scope of computer-readable memory 340 can further be used to store sensor data for any combination of sensors 310 in data store 342. Additionally, or alternatively memory 240 may be used to store medical-related data for the user.

Turning to the contents of the memory 340 in more detail, the memory 340, in at least one embodiment, includes an operating system 344 and one or more application programs, modules, or services for implementing the features disclosed herein including at least the perceived latency, such as via the faceplate device 112 or dedicated applications. In at least one example embodiment, the faceplate device 112 is configured to receive, store, and/or display content and at least one interface for interacting with the service provider computers 116 and users. Additionally, the memory 340 stores access credentials and/or other user information such as, but not limited to, user IDs, passwords, and/or other user information. In some examples, the user information includes information for authenticating an account access request such as, but not limited to, a device ID, a cookie, an IP address, a location, or the like. Additionally, the user information includes information regarding a therapy associated with the user.

The memory 340 of the faceplate device 112 also can comprise software elements (not shown), device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more processes described with respect to the method(s) discussed above might be implemented as code and/or instructions executable by the faceplate device 112 (and/or processing unit(s) 303 within a faceplate device 112) and/or stored on a non-transitory and/or machine-readable storage medium (e.g., a "computer-readable storage medium," a "machine-readable storage medium," etc.). In an aspect, then, such code and/or instructions can be used to configure and/or adapt a general purpose processor (or other device) to perform one or more operations in accordance with the described methods.

Faceplate device 112 may include clock 350. Clock 350 is used to generate a time stamp for each of the data observations generated by the sensors. The time stamps are used by the processing units 303 in the analysis of sensor data, and facilitate pattern recognition and improved capacity for determining the operational environment of the faceplate device 112 and wristband monitoring device 110. The clock 350 can also be used by the processing units 303 for alarms and other standard clock functions.

The faceplate device 112 includes a user interface 360. User interface 360 may include a touchscreen, a button or a keypad interface, a vibration generator, a sound generator, and/or other similar interface. The interface facilitates soliciting information from the wearer and obtaining input data and information provided by the wearer in response.

The faceplate device 112, using user interface 360, solicits information about the user or the user's condition or environment so as to analyze such data in order to provide the wellness monitoring features discussed herein. For example, the faceplate device 112 utilizes user inputs via user interface 360 to obtain information about the user's physique, lifestyle, health, activity level as well as information related to therapy compliance and other information relevant to ascertaining the user's overall wellness. The faceplate device 112 further solicits any inputs that may facilitate improved learning, analysis and sensing performed by the faceplate device 112, the wristband monitoring device 110, and/or other suitable devices or computers (e.g., service provider computers 116).

The faceplate device 112 includes an energy source, a means to charge said energy source, and a means to charge an energy source located on wristband monitoring device 110, indicated by power input/outputs 370. The energy source may be a battery, a capacitor, or any other suitable means for storing chemical or electrical energy for later use. In at least one embodiment, wristband monitoring device 110 may be connected to faceplate device 112 and the battery of the faceplate device 112 may charge the battery of wristband monitoring device 110.

In some embodiments, wristband monitoring device 110 may be connected to the faceplate device 112 and the battery of faceplate device 112 may be the energy source for the wristband monitoring device 110 or vice versa. The faceplate device 112 may be configured to charge from a standard A/C adaptor, or by use of a charging dock (e.g., a charging cradle) configured to house the faceplate device 112, or other suitable charging means.

Figure 4:
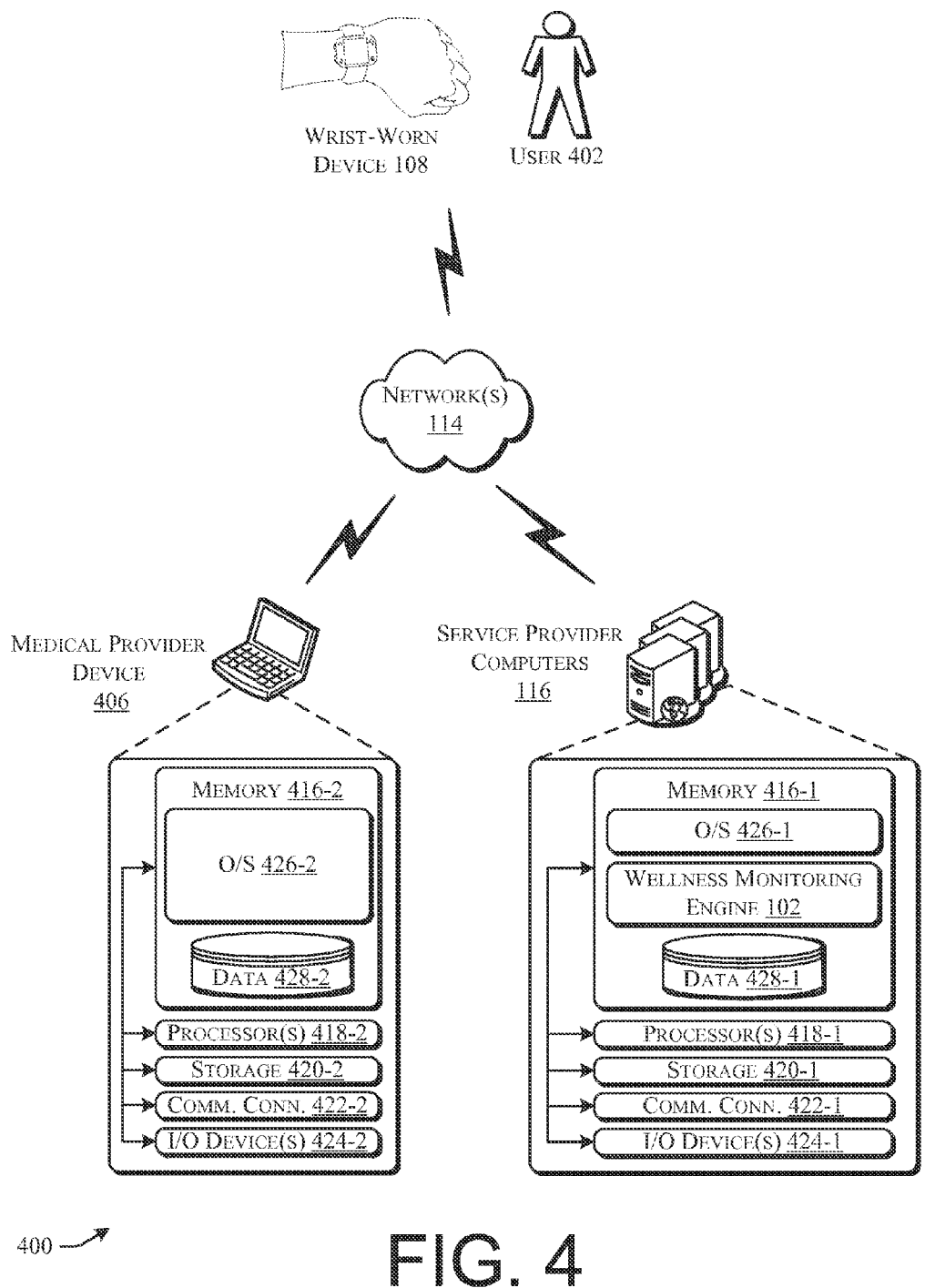
FIG. 4 depicts an example system or architecture for providing a wellness monitoring engine in accordance with at least one embodiment.

FIG. 4 depicts an example system or architecture 400 for monitoring wellness of a user of the wrist-worn device 108. Although wellness monitoring engine 102 is depicted as being located on service provider computers 116, wellness monitoring engine 102 may be located on any suitable device (e.g., the wrist-worn device 108, medical provider device 406). In architecture 400, a user 402 utilizes the wrist-worn device 108 (e.g., a wristband monitoring device 110 and a faceplate device 112) to access a wellness monitoring engine 102, or a user interface accessible by the wellness monitoring engine 102, via one or more networks 114. Wellness monitoring engine 102 may be hosted, managed, and/or provided by a computing resources service or service provider, such as by utilizing one or more service provider computers 116. The one or more service provider computers 116, in some examples, provide computing resources such as, but not limited to, client entities, low latency data storage, durable data storage, data access, management, virtualization, cloud-based software solutions, electronic content performance management, etc. The one or more service provider computers 116 are also operable to provide web hosting, computer application development, and/or implementation platforms, combinations of the foregoing, or the like to the user. In some embodiments, the wellness monitoring engine 102 is provided on the wrist-worn device 108.

In some examples, the wrist-worn device 108 is in communication with the service provider computers 116 via the networks 114, or via other network connections. Additionally, the wrist-worn device 108 may be part of a distributed system managed by, controlled by, or otherwise part of the service provider computers 116. In some examples, the networks 114 include any one or a combination of many different types of networks, such as cable networks, the Internet, wireless networks, cellular networks and other private and/or public networks.

In at least one embodiment, the wellness monitoring engine 102 allows the user 402 to interact with the service provider computers 116 or medical provider device 406. The one or more service provider computers 116, perhaps arranged in a cluster of servers or as a server farm, host the wellness monitoring engine 102 and/or cloud-based software services. Other server architectures may be used to host the wellness monitoring engine 102 and/or cloud-based software services. The wellness monitoring engine 102 is capable of handling requests from a user 402 and serving, in response, various user interfaces that are rendered at the wrist-worn device 108. The wellness monitoring engine 102 provides any type of device or application control. The wellness monitoring engine 102 and/or corresponding control are provided by the operating system 344 of the faceplate device 112. As discussed above, the described techniques can similarly be implemented outside of the wellness monitoring engine 102, such as with other applications running on the wrist-worn device 108.

In some aspects, the service provider computers 116 and medical provider device 406 are any type of computing devices such as, but not limited to, a mobile phone, a smart phone, a personal digital assistant (PDA), a laptop computer, a desktop computer, a server computer, a thin-client device, a tablet PC, etc. Additionally, it should be noted that in some embodiments, the service provider computers 116 and/or medical provider device 406 are executed by one or more virtual machines implemented in a hosted computing environment. The hosted computing environment may include one or more rapidly provisioned and released computing resources, which computing resources may include computing, networking and/or storage devices. A hosted computing environment is also referred to as a cloud-computing environment.

In one illustrative configuration, the service provider computers 116 and medical provider device 406 each include at least one memory (e.g., the memory 416-1 and the memory 416-2) and one or more processing units (e.g., processor(s) 418-1 and processor(s) 418-2). The processor(s) 418-1 and/or the processor(s) 418-2 are implemented as appropriate in hardware, computer-executable instructions, firmware, or combinations thereof. Computer-executable instruction or firmware implementations of the processor(s) 418-1 and the processor(s) 418-2 include computer-executable or machine-executable instructions written in any suitable programming language to perform the various functions described.

In at least one example embodiment, the memory 416-1 and/or the memory 416-2 store program instructions that are loadable and executable on the processor(s) 418-1 or the processor(s) 418-2, respectively, as well as data generated during the execution of these programs. Depending on the configuration and type of service provider computers 116 or medical provider device 406, the memory 416-1 and/or the memory 416-2 may be volatile (such as RAM) and/or non-volatile (such as ROM, flash memory, etc.). The service provider computers 116 and/or the medical provider device 406 also include additional storage (e.g., additional storage 420-1 and additional storage 420-2) which includes removable storage and/or non-removable storage. The memory 416-1, the memory 416-2, the additional storage 420-1, the additional storage 420-2, both removable and non-removable, are all examples of computer-readable storage media. In at least one example, computer-readable storage media include volatile or non-volatile, removable or non-removable media implemented in any method or technology for storage of information such as computer-readable instructions, data structures, program modules, or other data. Additional types of computer storage media that may be present in the service provider computers 116 and/or medical provider device 406 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the service provider computers 116 and/or medical provider device 406, respectively. Combinations of any of the above should also be included within the scope of computer-readable media.

In accordance with at least one embodiment, the service provider computers 116 and/or medical provider device 406 contain communications connection(s) (e.g., 422-1 and 422-2) that allow the service provider computers 116 and/or medical provider device 406 to communicate with a stored database, another computing device or server, user terminals and/or other devices on the networks 114. The service provider computers 116 and/or medical provider device 406 also include I/O device(s) 424-1 and/or I/O device(s) 424-2, respectively, such as a keyboard, a mouse, a pen, a voice input device, a touch input device, a display, speakers, a printer, etc.

Turning to the contents of the memory (e.g., the memory 416-1 and/or the memory 416-2) in more detail, each memory includes an operating system (e.g., 426-1 and 426-2), one or more data stores (e.g., 428-1 and 428-2), and/or one or more application programs, modules, or services for implementing the features disclosed herein. For example, medical-related data, sensor data collected from wrist-worn device 108, and any suitable data utilized by wellness monitoring engine 102 may be stored in data store 428-1 and/or data store 428-2.

Figure 5:
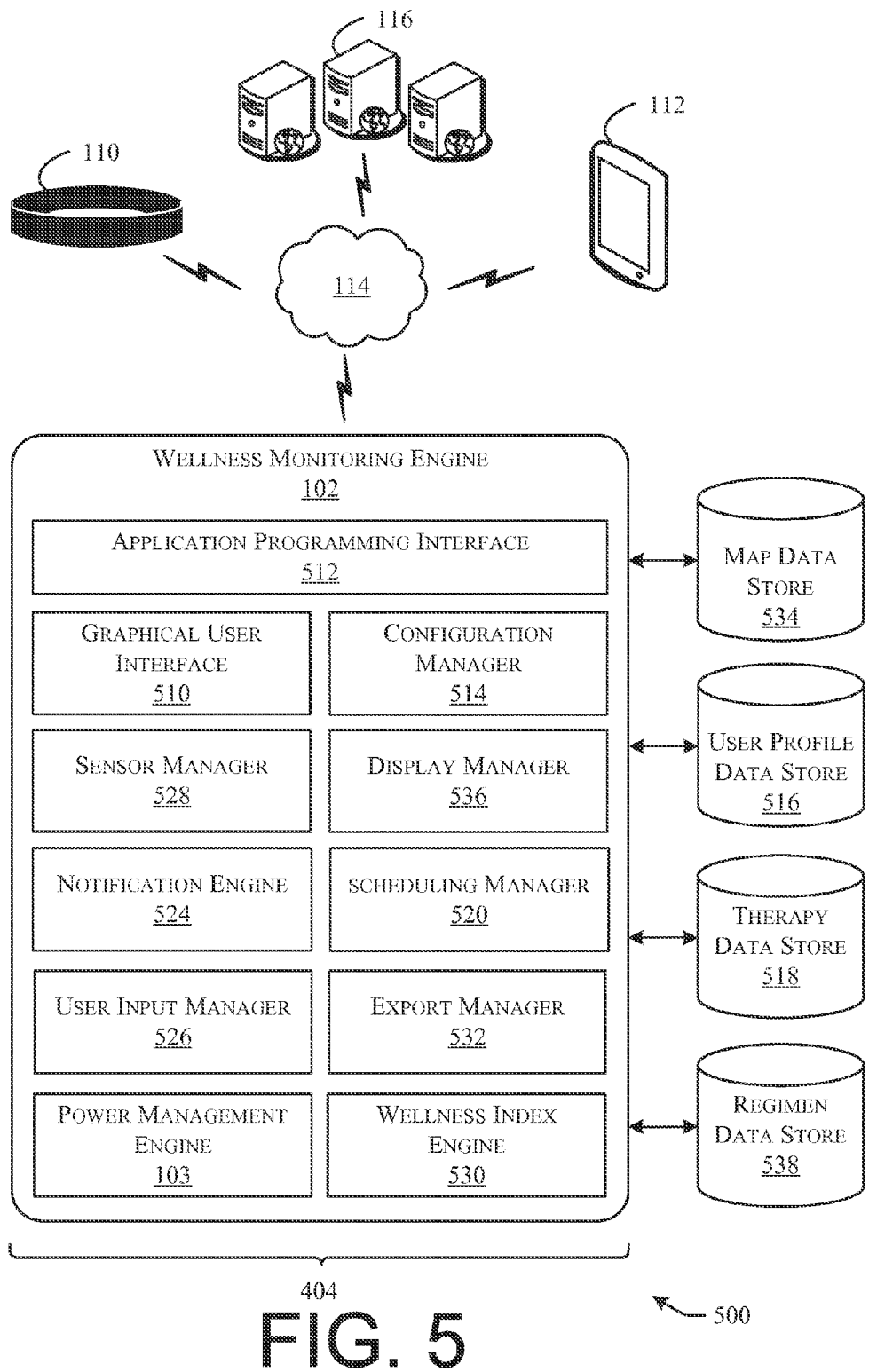
FIG. 5 depicts an example computer architecture for providing a wellness monitoring engine, including a power management engine that may carry out various embodiments.

FIG. 5 depicts an example computer architecture 500 for providing a wellness monitoring engine 102, including a plurality of modules 504 that may carry out various embodiments. Wellness monitoring engine 102 can be provided on wrist-worn device 108, medical provider device 406, service provider computers 116, or on another device in communication with the wrist-worn device 108 via network 114. In at least some examples, the modules 504 are software modules, hardware modules, or a combination thereof. If the modules 504 are software modules, the modules 504 are embodied on a computer-readable medium and processed by a processor in any of the computer systems described herein. It should be appreciated that any module or data store described herein, may be, in some embodiments, a service responsible for managing data of the type required to make corresponding calculations. The modules 504 may be configured in the manner suggested in FIG. 5 or may exist as separate modules or services external to the wellness monitoring engine 102.

In accordance with at least one embodiment, a method is enabled for wellness monitoring using a wrist-worn device (e.g. wrist-worn device 108). For example, the wellness monitoring engine 102 may be a component of the faceplate device 112, wristband monitoring device 110, or service provider computers 116 as discussed above in connection with FIGS. 2-4, respectively. In at least one embodiment, wellness monitoring engine 102 is stored on faceplate device 112 or, alternatively, is stored on a server accessible to the faceplate device 112 via network 114.

An administrator (e.g., a physician) configures the wellness monitoring engine 102 via a graphical user interface 510 the wellness monitoring engine 102 presented on medical provider device 406. Medical provider device 406 may be any electronic device capable of receiving and transmitting electronic data (e.g., a laptop, a cellphone, another wrist-worn device 108). The configuration information can include, but is not limited to, medical-related data. Once configuration information is entered via graphical user interface 510, application programming interface 512, a component of the wellness monitoring engine 102, is utilized to receive the configuration information.

In accordance with at least one embodiment, configuration manager 514, a component of the wellness monitoring engine 102, is configured to receive configuration information. The configuration manager 514 is responsible for creating and maintaining a user profile utilized to store such configuration information, including therapy or treatment information for the user. Further, the configuration manager 514 causes such configuration data to be stored in a user profile data store 516 (e.g., data store 242, data store 342, or data store 428-1). Additionally, or alternatively, configuration manager 514 interacts with therapy data store 518, a data store responsible for storing information regarding one or more therapies. In at least one example, the configuration manager 514 queries therapy data store 518 for information regarding one or more therapies indicated in the received configuration information. Any information returned from therapy data store 518 may be stored by the configuration manager 514 in user profile data store 516, along with, or separate from, the user profile.

In at least one embodiment, scheduling manager 520 is configured to receive configuration information from configuration manager 514, including information pertaining to a prescribed therapy. The prescribed therapy may be associated with a specific therapy stored in the therapy data store 518. The scheduling manager 520 is responsible for generating a regimen based on the prescribed therapy. The regimen indicates one or more notifications to be provided to the user at a specific day and/or time. The regimen additionally indicates one or more particular times at which to transmit medical-related information gathered or obtained by the wrist-worn device 108 to service provider computers 116. In at least one example, scheduling manager 520, according to the generated regimen, causes notification engine 524 to provide one or more electronic notifications on faceplate device 112. The notification may include, but is not limited to, a sensor reading request, to take a dosage of medication, or to conduct a form of exercise.

In at least one embodiment, user input manager 526 is configured to present questions to the user via faceplate device 112 of wrist-worn device 108. In at least one example, scheduling manager 520 determines one or more questions to be posed to the user at a particular time in accordance with the generated regimen. A "regimen," as used herein, includes a schedule for one or more therapies that specifies various times in which to conduct various actions associated with the therapy. In the case where the regimen specifies that a question should be posed to the user, scheduling manager 520 causes user input manager 526 to pose the determined question(s) to the user via faceplate device 112 at the appropriate time. The user utilizes faceplate device 112 to respond to the question(s). Upon receipt of the response, user input manager 526 stores such response data in user profile data store 516 (e.g., data store 242, 342, or 428-1). Additionally, user input manager 526 causes scheduling manager 520 to act upon the response in one or more ways based on the therapy implemented. In one example, scheduling manager 520, determining that it is time for the user to take a sensor reading, causes notification engine 524 to present a reminder to the user on faceplate device 112. The user input manager 526 sends to the device a question such as "are you ready to get your blood pressure taken?" The user responds affirmatively or negatively. Alternatively, the user, having had no question posed, affirmatively initiates, via faceplate device 112, a sensor reading. Either or both user inputs are received by user input manager 526. Additionally, such user input is stored in user profile data store 516 and is forwarded to scheduling manager 520. Scheduling manager 520, in response to such user input, updates the regimen.

In at least one example, scheduling manager 520 causes user input manager 526 to pose a question to the user via faceplate device 112. For instance, scheduling manager 520 determines that a question ought to be posed to the user at a particular time, or because of a particular response. For instance, the regimen may specify that the user be asked, "Are you feeling light-headed?" an hour after the user has indicated that he took his medication. In such a case, scheduling manager 520 causes user input manager 526 to present the question to the user via faceplate device 112. The user responds to the question via faceplate device 112 and such response is received by user input manager 526, stored in user profile data store 516 (e.g., data store 342 or data store 428-1), and/or forwarded to scheduling manager 520. In at least one embodiment, scheduling manager 520 updates the regimen based on the response. For example, the therapy may indicate that, if the user responds that he does, in fact, feel light-headed when asked (e.g., an hour after taking his medication), the regimen be altered in some way (e.g., by increasing or decreasing the medication dosage). In at least one example, the regimen is altered such that the user is immediately prompted to take an additional dosage. Furthermore, the regimen is updated by the scheduling manager 520 to reflect changes brought on by the received user input. The regimen may be stored on regimen data store 538 or any suitable data store configured to store such information. Regimen data store 538 may include as a component of wellness monitoring engine 102 or as a data store remote to wellness monitoring engine 102.

In at least one embodiment, a therapy may specify one or more times for which a sensor contained in the wrist-worn device 108 may be used to ascertain one or more patients' vital signs. For instance, a therapy specifies that the user's pulse and blood pressure should be taken once every hour. Such specifications are included in the regimen generated by scheduling manager 520. The therapy additionally, or alternatively, indicates certain chains of events that should result in activation of the sensor(s). For instance, a user is reminded to take his medication. He, in fact, takes the medication and responds to the reminder, or a posed question, indicating that he took his medication. Upon this input, or some time later, scheduling manager 520 causes sensor manager 528, a component of wellness monitoring engine 102, to activate one or more sensors located on the wrist-worn device 108. Sensor manager 528 communicates with the one or more sensors to cause vital sign information to be collected. For instance, in the ongoing example, sensor manager 528 causes a heart rate sensor to be activated. The sensor manager 528 is configured to receive data from the heart rate sensor. The sensor manager 528 further causes the heart rate information to be stored in user profile data store 516 and/or forwards the heart rate information to the scheduling manager 520 for analysis. Sensor manager 528, additionally or alternatively, activates blood pressure sensor. The sensor manager 528 is configured to receive data from the blood pressure sensor. The sensor manager 528 causes the blood pressure sensor to be stored in user profiled data store 516 and/or forwards the blood pressure information to the scheduling manager 520. Scheduling manager 520, as discussed above, analyzes the heart rate information and/or the blood pressure information to determine any regimen modification(s) necessary in accordance with the therapy. Though a heart rate sensor and a blood pressure sensor are used in this example, it should be appreciated that any sensor, or combination of sensors, located on the wristband monitoring device 110 or faceplate device 112 may be utilized, in any suitable order, via a similar manner as described above.

Consider the case where the user's heart rate drops dangerously low, or even stops. The sensor manager 528 can receive such information and determine that the rate is in an unacceptable range as defined by the therapy. Upon such a determination, the sensor manager 528 can cause notification engine 524, or any other suitable component of the wellness monitoring engine 102, to access the user profile data store 516 for user profile data. User profile data indicates physician contact information and/or emergency contact information, for example. If the user profile data includes such information, the notification engine 524 may cause a notification to be sent to the indicated physician/emergency contact. In at least one example, the notification includes an automated phone call, email message, text message, or other suitable form of communication. Additionally, or alternatively, the notification engine 524 can transmit data related to the adverse condition (e.g., sensor data, user profile data) to an emergency response unit. In one example, upon determining the existence of an adverse condition, the sensor manager 528 causes the GPS sensor to activate to ascertain the user's location. Any other sensor, or combination of sensors, included on the device may be similarly activated. Information collected by the sensor(s) is received by the sensor manager 528. The sensor manager 528 can relay the information to notification engine 524. Notification engine 524 may then report such information away from the device in a manner similar to that described above.

In at least one embodiment, the user may activate a setting on the device to indicate an emergency status. For example, the user may be aware that they are having a health issue and interact with a user interface (e.g., user interface 360) located on the faceplate device 112. The indication is received by the user input manager 526. User input manager is configured to access user profile data store 516 to obtain user profile data in order to determine contact information similar to that described in the previous example. User input manager 526 is configured to cause notification engine 524 to notify the determined contacts and/or emergency response unit(s).

In at least one embodiment, another user, for example a physician or emergency medical personnel, may access medical-related data stored in memory 416-1 of service provider computers 116 or other information contained on and/or recorded by wrist-worn device 108. For example, in an emergency situation, another user can access medical allergy information of the user. Additionally, or alternatively, someone other than the user may access information recorded by the wrist-worn device 108. As an example, a physician can enable medical-related data to be displayed on the faceplate device 112 or a display of another device. The activation of such a setting is received by the user input manager 526. The user input manager 526 accesses user profile data store 516 to obtain medical-related data for the user. The user input manager 526 can then display such information on the faceplate device 112 and/or enable the physician to access such information at a remote location (e.g., via a website presented on the medical provider device 406 or other computing device).

In accordance with at least one embodiment, scheduling manager 520 determines, based on the current regimen, user input, or sensor data, that medical-related data (e.g., user input, user responses, vital sign information) should be sent to a medical provider (e.g., the prescribing physician). Additionally, or alternatively, scheduling manager 520 receives input requesting the medical-related data. In either case, scheduling manager 520 causes export manager 532 to electronically transmit the medical-related data to a particular location. In at least one example, the medical-related data is displayed (e.g., via notification engine 524) on a medical provider's device (e.g., medical provider device 406).

In accordance with at least one embodiment, wellness index engine 530, a component of wellness monitoring engine 102, is responsible for calculating a wellness index for the patient. The wellness index, as described above, is a numerical value that indicates an overall wellness value for the patient. The wellness index engine 530 may be configured to receive, or otherwise obtain, at least one of sensor data, therapy data, regimen, or user input, from any combination of the modules discussed above. Therapy data may include information related to normal sensor data ranges (e.g., a normal heart rate range, normal glucose level). Such normal sensor data ranges may be based on age, sex, race, or other suitable demographic information. Upon receipt, or at a suitable time, the wellness index engine 530 may calculate a wellness index based on the sensor data, therapy data, regimen data, and user input and store the calculated value in user profile data store 516. The wellness index may be calculated using various weights for the sensor data, therapy data, regimen, and user input or each may be weighed the same for purposes of the calculation. In at least one example, wellness index engine 530 may interact with user profile data store 516 to retrieve information regarding medical-related data of other users. For example, the wellness index engine 530 may take into account other users blood pressure readings, for example, when determining how much weight to give the user's blood pressure reading. Wellness index engine 530 may take into account all other users, or a subset of the other users. For example, wellness index engine 530 may compare the user's blood pressure readings to other user's under the same proscribed therapy, while ignoring medical-related data of users that are not under the same prescribed therapy.

Wellness index engine 530 may be configured to cause export manager 532 to transmit the wellness index to wrist-worn device 108, the medical provider device 406, service provider computers 116, or any suitable electronic device located away from wellness monitoring engine 102.

In at least one embodiment, display engine 536, a component of wellness monitoring engine 102, may be configured to interact with map data store 534 in order to display a map of a geographical location (e.g., a hospital ward floor plan, assisted living home floor plan, a region map, a state map). In at least one example, the display engine 536 may cause a floor plan of a hospital ward to be displayed, for example, on medical provider device 406), with, in some cases, at least one graphical element (e.g., a colored dot) superimposed over the floor plan indicating a location and wellness index generated by a wrist-worn device (e.g., a wrist-worn device worn by a patient of the hospital).

In at least one embodiment, power management engine 103, a component of wellness monitoring engine 102, may be configured to monitor power consumption of faceplate device 112 and power consumption of wristband monitoring device 110. For example, power management engine 103 may interact with display engine 536 to cause power levels of the faceplate device 112 and wristband monitoring device 110 to be displayed (e.g., on faceplate device 112). In some cases, the power levels displayed may be provided on the faceplate device 112 as a graphical element (e.g., a battery icon for each the faceplate device 112 and the wristband monitoring device 110). In some examples, the power level for wristband monitoring device 110 may be provided via lights located on wristband monitoring device 110. Such lights, or even the wristband itself, may flash and/or change color depending on the power level remaining for the wristband monitoring device 110.

In accordance with at least one embodiment, power management engine 103 may receive indication that the faceplate device 112 has been detached from wristband monitoring device 110. Upon receiving such an indication, power management engine 103 may track power usage of wristband monitoring device 110. Depending on the regimen and the power level remaining for the wristband monitoring device 110, power management engine 103 may interact with scheduling manager 520 to cause updates to the regimen. For example, power management engine 103 may cause sensor readings to be taken less frequently than a frequency at which sensor readings would have been taken if the wristband monitoring device 110 was attached to the faceplate device 112, or alternatively, if the wristband monitoring device 110 was operating at full power strength.

In accordance with at least one embodiment, power management engine 103 may interact with notification engine 524 to cause audible alerts to sound on either, or both, the faceplate device 112 or wristband monitoring device 110. For example, power management engine 103 may determine that faceplate device 112 has a remaining power level under a threshold amount (e.g., 10 percent or less of total power available). Based on the determination, power management engine may interact with notification to sound an audible alarm on the faceplate device 112. Similarly, may determine that wristband monitoring device 110 has a remaining power level under a threshold amount (e.g., 10 percent or less of total power available). The threshold amount may be the same, or different, than the threshold amount used in the previous example. Based on the determination, power management engine may interact with notification to sound an audible alarm on the wristband monitoring device 110. The sound of the alarm on wristband monitoring device 110 may be the same, or different, than the sound of the alarm on faceplate device 112.

In accordance with at least one embodiment, power management engine 103 may track the power usage of either, or both, the power source(s) located on faceplate device 112 or wristband monitoring device 110. Such tracked information may be communicated to export manager 532 in order to transmit such information away from the wrist-worn device (e.g., to a remote server configured to analyze such information). Additionally, or alternatively, export manager 532 may store tracked power source usage history in user profile data store 516, associated with the user's profile.

Figure 6:
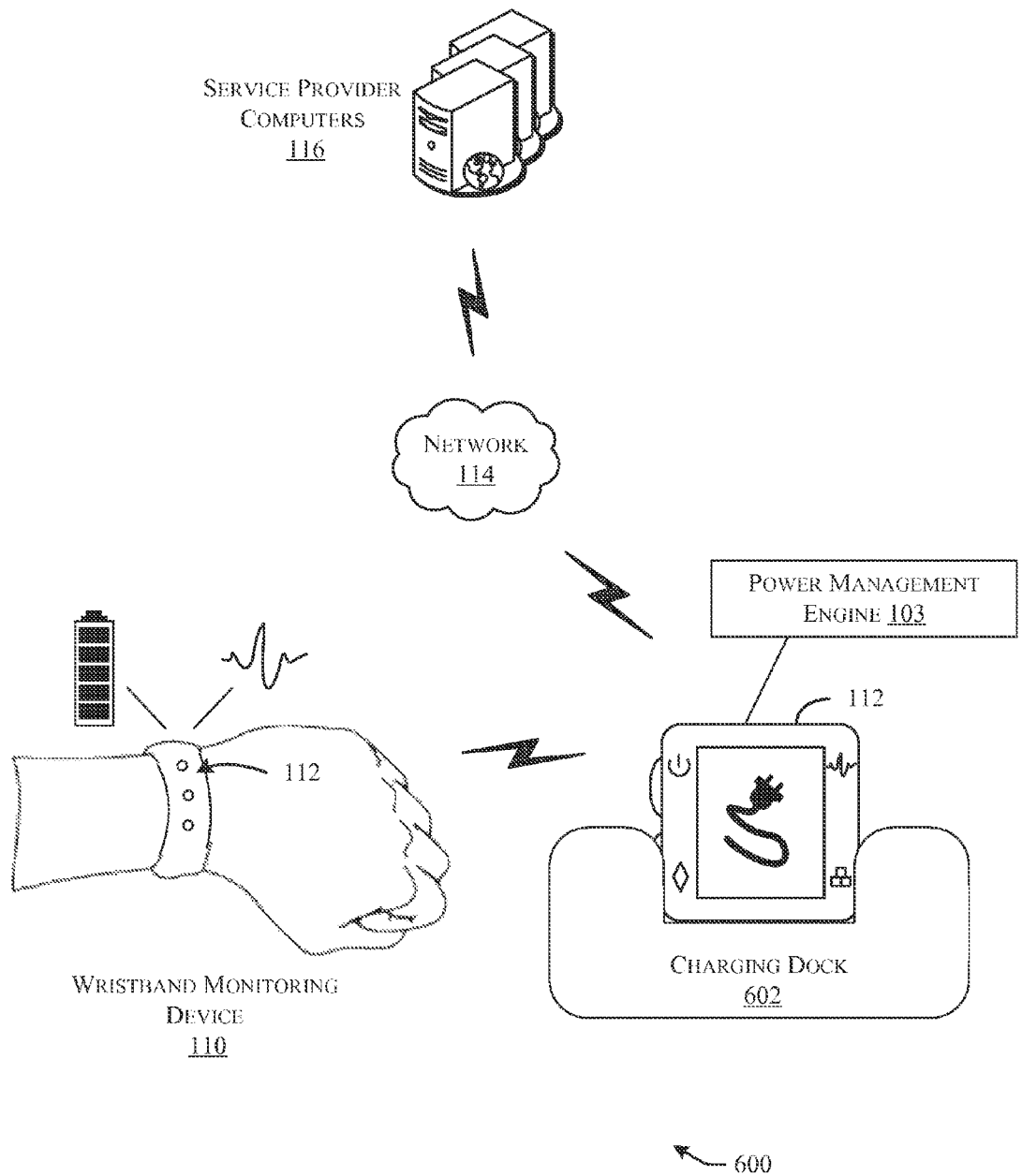
FIG. 6 depicts an example of another embodiment of a power management engine.

FIG. 6 depicts an example of another embodiment 600 of a power management engine 103. The faceplate device 112 may include a power management engine 103. In accordance with at least one embodiment, the wrist-worn device 108, including the wristband monitoring device 110 and faceplate device 112, may be pre-configured with a prescribed therapy (e.g., by a medical provider device 406).

In accordance with at least one embodiment, the user may decide to detach the faceplate device 112 from the wristband monitoring device 110. For example, the faceplate device 112 may be detached in order to charge the faceplate device 112 using charging dock 602. Although a charging dock is depicted, any suitable form of charging may be substituted. For example, while the faceplate device 112 may be charged via a charging dock, the wristband monitoring device 110 may be charged utilizing a form of wireless charging (e.g., inductive charging using magnetic or acoustic methods). In another example, both the faceplate device 112 and the wristband monitoring device 110 may be charged using an inductive charger. The wristband monitoring device 110 may include one or more sensors with which to monitor a patient's vital signs (e.g., using sensors 210). The wristband monitoring device 110 may continue monitoring vital signs while the faceplate device 112 is detached and charging. While detached, the wristband monitoring device may operate using, for example, battery power. Battery power levels and/or sensor activity may be indicated by LED lights 604 located on the wristband monitoring device or any suitable visual or audible means of indication. In at least one example, low battery power may cause LED lights 604 to flash red while a sensor reading may cause the LED lights 604 to flash blue.

In accordance with at least one embodiment, wristband monitoring device 110 may wirelessly transmit sensor readings to faceplate device 112. Such transmission may be accomplished using Bluetooth or any suitable means for wireless transmission. While detached, faceplate device 112 may continue to transmit vital sign information away from the wrist-worn device 108. Alternatively, or additionally, faceplate device 112 may transmit medical-related data away from wrist-worn device 108. While attached, or detached, faceplate device 112 may display power levels of wristband monitoring device 110, for example, using user interface 360. Such display may include a battery icon indicating the remaining power levels of wristband monitoring device 110. While charging, otherwise, faceplate device 112 may display power levels of the faceplate device 112, for example, using user interface 360. Such display may include a battery icon indicating the remaining power levels of faceplate device 112.

In at least one embodiment, the wellness monitoring engine 102 is a component of the wrist-worn device 108.

Figure 7:
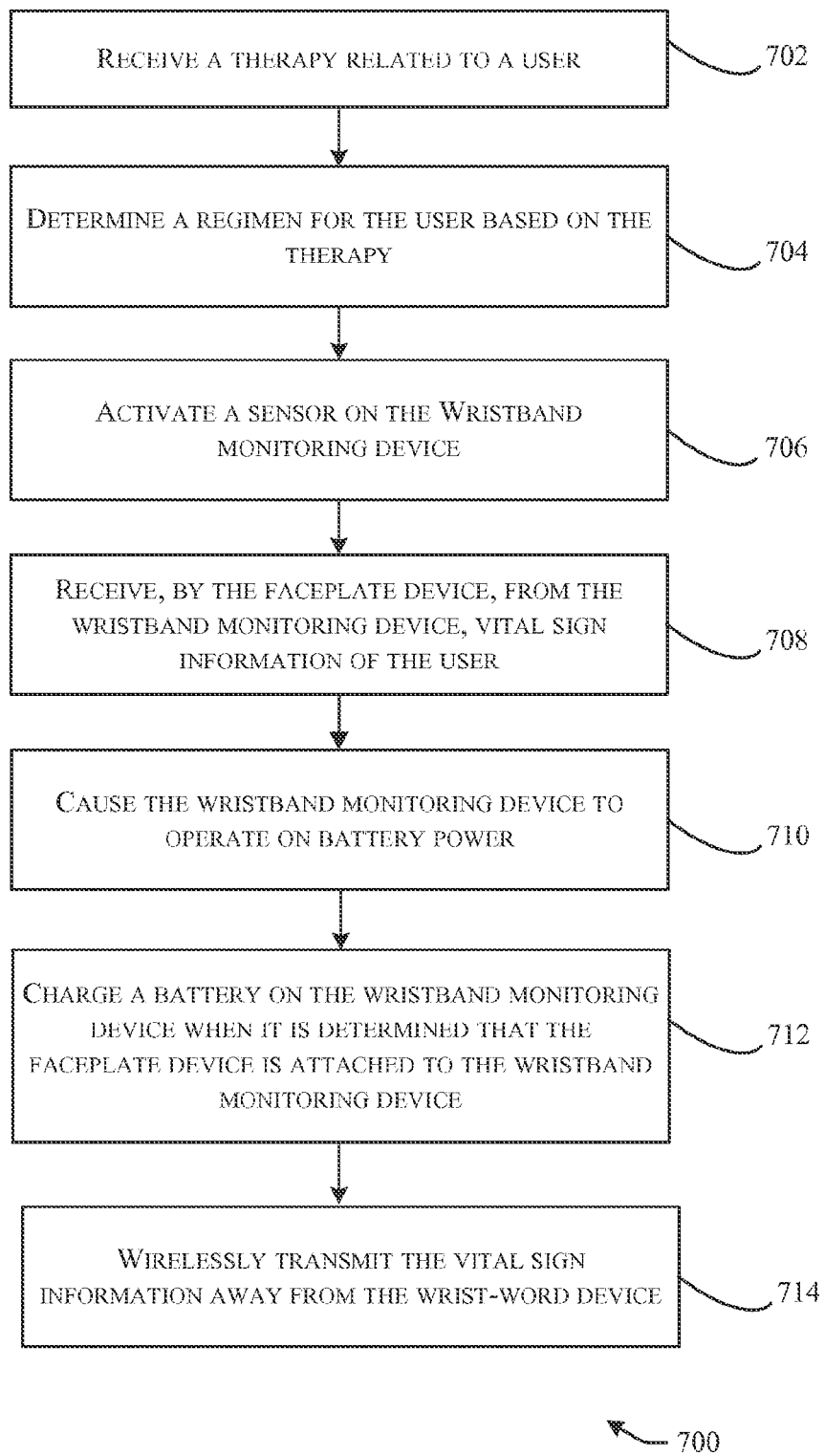
FIG. 7 depicts a flowchart of an example method for using the power management engine.

FIG. 7 depicts a flowchart of an example method 700 for using the power management engine 103. The flow chart 700 begins at 702, where a therapy related to a user is received by wrist-worn device 108. As described above, a "therapy" includes, but is not limited to, one or more prescribed medications, one or more physical activities, one or more sensor requests, or any combination of the above. A user is a patient recipient of the therapy. The therapy is received by the wrist-worn device 108, or more specifically, by the faceplate device 112.

At 704, a regimen for the user is determined based on the therapy. For instance, the regimen is determined by the scheduling manager 520 of FIG. 5 in the manner described above. Alternatively, the regimen is determined by retrieving a previously store regimen from therapy data store 518 of FIG. 5. As described above, the regimen specifies at least one situation for which at least one event associated with a therapy should be performed. For instance, a regimen indicates that an event (e.g. sensor data collection) should occur at pre-determined periodic times. In at least one example, the regimen indicates that an event (e.g., a blood pressure sensor reading) ought to occur in response to a particular received input (e.g., indication that the patient wishes to take his blood pressure). A variety of situations exist and would depend on the therapy being implemented.

At 706, a sensor (e.g., one or more of sensors 210) may be activated on the wristband monitoring device 110. For example, blood pressure monitor sensor 220 may be activated. The blood pressure monitor sensor 220 may be activated based on the determined regimen from 704. In cases where the faceplate device 112 is detached from the wristband monitoring device 110. The sensor activation may further depend on a power level remaining on the wristband monitoring device 110. For example, a regimen may specify that a blood pressure reading should be taken once every four hours. If the wristband monitoring device 110 is operating at approximately full power (e.g., 90% or above of total power capacity) then the readings may continue to occur every four hours. At some point, the power level remaining on the wristband monitoring device 110 may drop below a threshold amount (e.g., 60% of total power capacity). At such time, power management engine 103 may cause an update to the regimen that causes blood pressure readings to be taken less frequently (e.g., every 5 hours) in order to conserve power on the wristband monitoring device 110.

At 708, vital sign information of the user may be received by faceplate device 112, from wristband monitoring device 110. In at least one example, wristband monitoring device 110 may transmit, wirelessly or otherwise, vital sign information to faceplate device 112. For instance, wristband monitoring device 110 may transmit vital sign information over Bluetooth to faceplate device 112.

At 710, wristband monitoring device 110 may be caused to operate on battery power (e.g., as a result of faceplate device 112 being detached). At such time, wristband monitoring device 110 may display status related to the power level of wristband monitoring device 110 on wristband monitoring device 110. As depicted in FIG. 6, the status may be displayed by LED light located on the wrist band of the wristband monitoring device 110. Additionally, or alternatively, the wristband itself may change color in order to display the status related to the power level of the wristband monitoring device 110.

At 712, a battery on the wristband monitoring device 110 may be charged. For example, when it is determined that the faceplate device 112 is attached to the wristband monitoring device 110, power management engine 103 may cause a power source of wristband monitoring to be charged from a power source located on faceplate device 112.

At 714, faceplate device 112 may wirelessly report the vital sign information away from the wrist-worn device 108. Alternatively, or additionally, medical-related data may be wirelessly reported away from the faceplate device 112. In at least one example, the medical-related data is reported to service provider computers 116 and/or medical provider device 406. Alternatively, the information may be sent wirelessly, to a physician via email.

Figure 8:
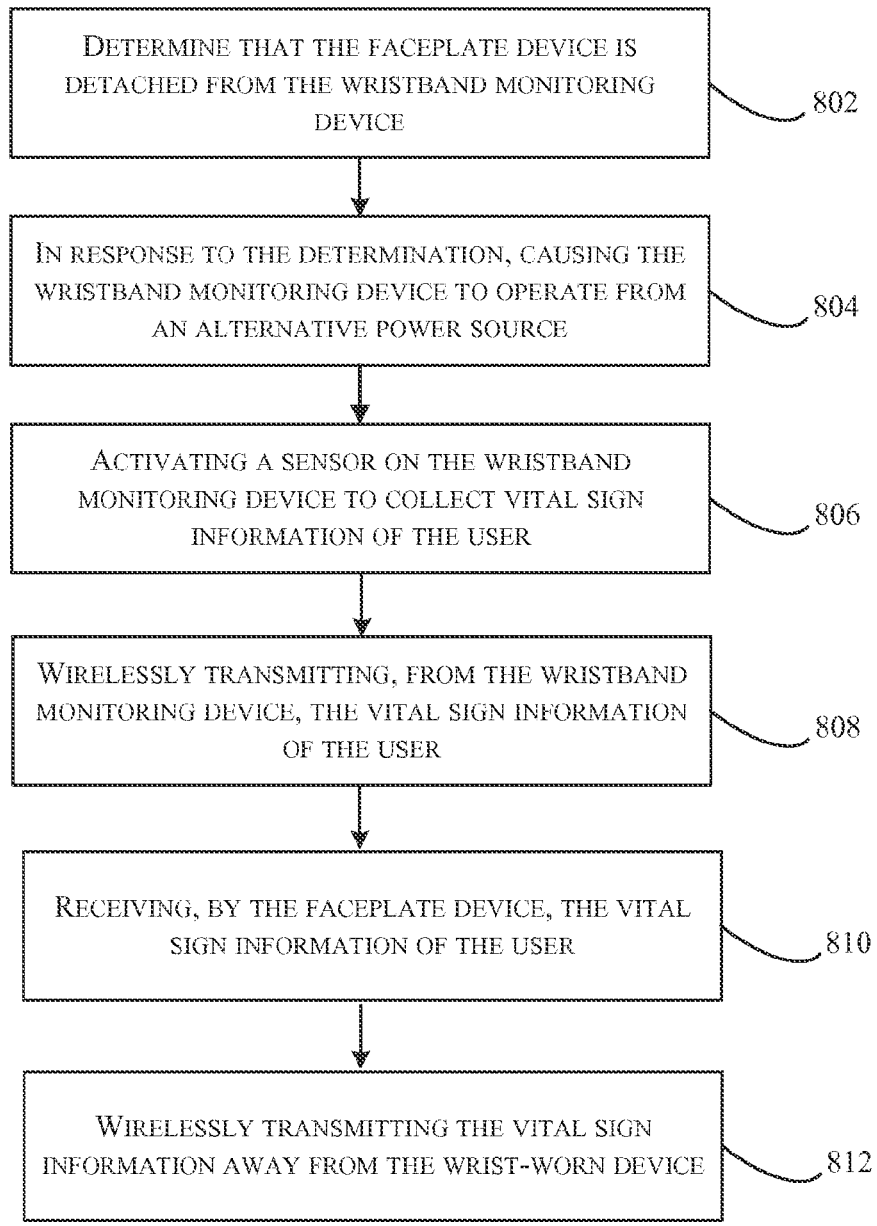
FIG. 8 depicts a flowchart of another example method for using the power management engine.

FIG. 8 depicts a flowchart of another example method for using the power management engine. The flow chart 800 begins at 802, where a determination that the faceplate device 112 is detached from the wristband monitoring device 110. Detachment could occur because the faceplate device 112 is being charged, or because the user wishes to wear only the wristband monitoring device 110, or for any suitable reason for detachment.

At 804, in response to the determination from 802, the wristband monitoring device 110 may be caused to operate from an alternative power source (e.g., from battery power). For example, power management engine 103 may cause the wristband monitoring device 110 to begin operating under battery power.

At 806, a sensor (e.g., blood pressure sensor(s) 220) on the wristband monitoring device 110 may be activated to collect vital sign information of the user. The activation may be based on a regimen as described above. The activation may occur during a time when the faceplate device 112 is detached from the wristband monitoring device 110.

At 808, vital sign information (e.g., blood pressure sensor readings) may be wirelessly transmitted from the wristband monitoring device. At 810, the faceplate device 112 may receive the vital sign information of the user. In some cases, the vital sign information may be received by the faceplate device 112 from the wristband monitoring device 110 via a Bluetooth connection.

At 810, the vital sign information may be wirelessly transmitted away from the wrist-worn device 108 (e.g., using export manager 532). For example, faceplate device 112 may transmit such data to service provider computers 116.

Implementation of the techniques, blocks, steps, and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodied instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read-only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to, portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A wrist-worn device for managing patient wellness, comprising:
one or more processors; and
one or more memories coupled with said one or more processors, wherein the one or more processors and the one or more memories are configured to:
receive, by the wrist-worn device, a therapy for a user, wherein the therapy specifies one or more treatments selected by a care provider, and wherein the wrist-worn device includes a wristband monitoring device and a faceplate device;
determine, by the wrist-worn device, a regimen for the user based on the therapy;
activate a sensor on the wristband monitoring device to collect vital sign information of the user, wherein activating the sensor is based on the regimen;
receive, by the faceplate device, from the wristband monitoring device, the vital sign information of the user;
cause the wristband monitoring device to operate on battery power when it is determined that the faceplate device is detached from the wristband device;
charge a battery on the wristband monitoring device from a battery on the faceplate device when it is determined that the faceplate device is attached to the wristband monitoring device; and
wirelessly transmit the vital sign information away from the wrist-worn device.

2. The wrist-worn device for managing patient wellness of claim 1, wherein the one or more processors and the one or more memories are further configured to:
generate, by the wrist-worn device, a notification related to a wellness concern; and
receive, by the wrist-worn device, affirmative user input related to a wellness concern.

3. The wrist-worn device for managing patient wellness of claim 1, wherein the one or more processors and the one or more memories are further configured to:
determining that the faceplate device has a remaining battery power level under a threshold amount; and
providing, on the faceplate device, an indication of the remaining battery power level.

4. The wrist-worn device for managing patient wellness of claim 1, wherein the indication of the remaining battery power level includes at least one of a visual display or an audible alert.

5. The wrist-worn device for managing patient wellness of claim 1, wherein the one or more processors and the one or more memories are further configured to:
determine that the faceplate device is detached from the wristband monitoring device, wherein activating the sensor on the wristband monitoring device is further based on the determination that the faceplate device is detached from a mounting device.

6. The wrist-worn device for managing patient wellness of claim 1, wherein charging the battery on the wristband monitoring device is further based on determining that the wristband monitoring device has a remaining battery level under a threshold amount.

7. A method for managing patient wellness with a wrist-worn device, the wrist-worn device including a wristband monitoring device and a faceplate device, comprising:
  determining that the faceplate device is detached from the wristband monitoring device;
  in response to the determination, causing the wristband monitoring device to operate on battery power;
  activating a sensor on the wristband monitoring device by the faceplate device;
  in response to the activating, collecting vital sign information of a user by the wristband monitoring device;
  wirelessly transmitting the vital sign information of the user from the wristband monitoring device to the faceplate device;
  receiving, by the faceplate device, the vital sign information of the user;
  determining that the faceplate device is attached to the wristband monitoring device; and
  in response to determining that the faceplate device is attached, charging a battery on the wristband monitoring device from a battery on the faceplate device.

8. The method for managing patient wellness with the wrist-worn device of claim 7, wherein the wristband monitoring device includes at least one of a thermometer, a pedometer, a blood pressure monitor, a heart rate sensor, a blood-oxygen level sensor, a global positioning satellite sensor, or a glucose monitor.

9. The method for managing patient wellness with the wrist-worn device of claim 7, wherein the vital sign information is transmitted to the faceplate device.

10. The method for managing patient wellness with the wrist-worn device of claim 7, further comprising:
  determining that the vital sign information of the user indicates an emergency situation; and
  providing, on the wristband monitoring device, an indication of the emergency situation.

11. The method for managing patient wellness with the wrist-worn device of claim 10, wherein the indication of the emergency situation is visually depicted on the wristband monitoring device.

12. The method for managing patient wellness with the wrist-worn device of claim 10, further comprising:
  wirelessly transmitting, from the faceplate device, the indication of the emergency situation away from the wrist-worn device.

13. A non-transitory computer-readable storage medium for managing patient wellness with a wrist-worn device, the wrist-worn device including a wristband monitoring device and a faceplate device, the non-transitory computer-readable storage medium having stored thereon computer-executable instructions that, when executed by a processor, cause the processor to perform operations comprising:
  determining that the faceplate device is detached from the wristband monitoring device;
  in response to the determination, causing the wristband monitoring device to operate from an alternative power source;
  activating a sensor on the wristband monitoring device to collect vital sign information of a user;
  activating a sensor on the wristband monitoring device by the faceplate device;
  in response to the activating, collecting the vital sign information of the user by the wristband monitoring device;
  wirelessly transmitting the vital sign information of the user from the wristband monitoring device to the faceplate device;
  receiving, by the faceplate device, the vital sign information of the user, and wirelessly transmitting the vital sign information from the wrist-worn device.

14. The non-transitory computer-readable storage medium of claim 13, having further computer-executable instructions that, when executed by the processor, cause the processor to perform further operations comprising:
  determining that the faceplate device is attached to the wristband monitoring device; and
  sending instructions to cause a battery on the wristband monitoring device to be charged, using an inductive charging technique, when it is determined that the faceplate device is attached to the wristband monitoring device.

15. The non-transitory computer-readable storage medium of claim 13, having further computer-executable instructions that, when executed by the processor, cause the processor to perform further operations comprising:
  determining, by the faceplate device, that the faceplate device is connected to a charging source; and
  providing an indication of charging on the faceplate device according to the determination.

16. The non-transitory computer-readable storage medium of claim 13, having further computer-executable instructions that, when executed by the processor, cause the processor to perform further operations comprising:
  determining, by the faceplate device, a power level associated with the wristband monitoring device; and
  providing, on the faceplate device, an indication of the power level associated with the wristband monitoring device.

17. The non-transitory computer-readable storage medium of claim 13, having further computer-executable instructions that, when executed by the processor, cause the processor to perform further operations comprising:
  tracking power usage history of the faceplate device; and
  wirelessly transmitting the battery usage history of the faceplate device away from the wrist-worn device.

18. The non-transitory computer-readable storage medium of claim 13, having further computer-executable instructions that, when executed by the processor, cause the processor to perform further operations comprising:
  receiving, by the faceplate device, power usage information of the wristband monitoring device; and
  wirelessly transmitting the power usage information of the wristband monitoring device away from the wrist-worn device.

19. The non-transitory computer-readable storage medium of claim 13, wherein the sensor on the wristband monitoring device is activated by the faceplate device utilizing a wireless transmission.

20. The wrist-worn device for managing patient wellness of claim 1, further comprising:
  determining that the faceplate device is detached from the wristband monitoring device; and
  in response to determining that the faceplate device is detached, modifying a frequency at which the sensor is activated on the wristband monitoring device.

* * * * *